United States Patent
Schlegel et al.

(10) Patent No.: US 8,954,129 B1
(45) Date of Patent: Feb. 10, 2015

(54) WEARABLE FOR ACQUISITION OF RESTING MULTI-LEAD ECG

(76) Inventors: Todd T. Schlegel, Houston, TX (US); Aaron T. Rood, Rocky River, OH (US)

(*) Notice: Subject to any disclaimer, the term of this patent is extended or adjusted under 35 U.S.C. 154(b) by 409 days.

(21) Appl. No.: 13/229,715

(22) Filed: Sep. 10, 2011

(51) Int. Cl.
*A61B 5/0408* (2006.01)
*A61B 5/00* (2006.01)

(52) U.S. Cl.
CPC ........... *A61B 5/0408* (2013.01); *A61B 5/04085* (2013.01); *A61B 5/6804* (2013.01); *A61B 5/6805* (2013.01); *A61B 5/6823* (2013.01)
USPC ............ 600/389; 600/382; 600/509; 600/393

(58) Field of Classification Search
CPC ............... A61B 5/0402; A61B 5/0408; A61B 5/04082; A61B 5/05085; A61B 5/6801; A61B 5/6802; A61B 5/6804; A61B 5/6805; A61B 5/6832; A61B 5/6824; A61B 5/683; A61B 5/6831; A61B 5/6834; A61B 5/6843; A61B 2562/164
USPC .......... 600/372, 382, 384, 386–390, 393, 509
See application file for complete search history.

(56) References Cited

U.S. PATENT DOCUMENTS

| | | | | |
|---|---|---|---|---|
| 3,409,007 | A * | 11/1968 | Fuller | 600/382 |
| 3,534,727 | A * | 10/1970 | Roman | 600/389 |
| 4,608,987 | A | 9/1986 | Mills | |
| D313,652 | S | 1/1991 | Lavine | |
| 5,224,479 | A | 7/1993 | Sekine | |
| 5,370,116 | A * | 12/1994 | Rollman et al. | 600/382 |
| 5,465,727 | A * | 11/1995 | Reinhold, Jr. | 600/523 |
| 6,065,154 | A * | 5/2000 | Hulings et al. | 2/102 |
| 6,205,346 | B1 | 3/2001 | Akiva | |
| 6,341,229 | B1 | 1/2002 | Akiva | |
| 6,408,200 | B1 | 6/2002 | Takashina | |
| 6,471,087 | B1 * | 10/2002 | Shusterman | 221/2 |

(Continued)

OTHER PUBLICATIONS

Welinder et al. "Differences in QRS Axis Measurements, Classification of Inferior Myocardial Infarction, and Noise Tolerance for 12-Lead Electrocardiograms Acquired From Monitoring Electrode Positions Compared to Standard Locations" Am. J. Cardio. 106 pp. 581-586 (2010).*

(Continued)

*Primary Examiner* — Lee S. Cohen
*Assistant Examiner* — Erin M Cardinal
(74) *Attorney, Agent, or Firm* — Brian Kolkowski; Robert Knecht Schmidt

(57) ABSTRACT

An electrode wearable or harness permits for easy, quick, and unsupervised administration or self-administration of a resting 12-or-more-lead ECG. Various advantageous features of the electrode wearable or harness include: inflatable or padded cushions at the lateral sides of the torso that function to press LA and RA electrodes mounted on the cushions against the downward-resting arms of the subject, permitting good electrode abutment with distal electrode placement without the need for adhesives, straps, bands, bracelets, or gloves on the arms; padding over the sternum to avoid tenting in the $V_1$, $V_2$, $V_3$ and $V_{3R}$ electrodes whenever present, easy-to-don, one-piece design with an adjustable single point of connection and an adjustable shoulder strap; Lund or modified Lund placement; dry electrodes; and various other features. Methods of use are also described.

19 Claims, 9 Drawing Sheets

(56) References Cited

U.S. PATENT DOCUMENTS

| | | | |
|---|---|---|---|
| 6,516,289 B2 | 2/2003 | David | |
| 6,847,836 B1 | 1/2005 | Sujdak | |
| 7,266,405 B1 | 9/2007 | Alroy | |
| 7,308,294 B2 | 12/2007 | Hassonjee | |
| 7,966,052 B2 * | 6/2011 | DeFusco et al. | 600/386 |
| 2002/0111777 A1 * | 8/2002 | David | 702/189 |
| 2004/0176674 A1 * | 9/2004 | Nazeri | 600/382 |
| 2005/0275416 A1 * | 12/2005 | Hervieux et al. | 324/663 |
| 2006/0069320 A1 | 3/2006 | Wolff | |
| 2007/0083096 A1 * | 4/2007 | Paradiso | 600/388 |
| 2007/0219454 A1 | 9/2007 | Guzzetta | |
| 2008/0064970 A1 | 3/2008 | Montplaisir | |
| 2008/0114232 A1 | 5/2008 | Gazit | |
| 2008/0161707 A1 * | 7/2008 | Farringdon et al. | 600/509 |
| 2008/0208029 A1 * | 8/2008 | Thijs et al. | 600/388 |
| 2008/0287770 A1 | 11/2008 | Kurzweil | |
| 2010/0191090 A1 | 7/2010 | Shin | |
| 2011/0004088 A1 | 1/2011 | Grossman | |
| 2012/0136231 A1 * | 5/2012 | Markel | 600/388 |

OTHER PUBLICATIONS

Schlegel, "Accuracy of advanced versus strictly conventional 12-lead ECG for detection and screening of coronary artery disease, left ventricular hypertrophy and left ventricular systolic dysfunction", BMC Cardiovascular Disorders, Jun. 2010, 10:28.

Bharadwaj, "Accurate ECG signal processing", EE Times Design, Feb. 2011, http://www.eetimes.com/design, http://www.cypress.com/?docID=28762.

Jowett, "Modified electrode placement must be recorded when performing 12-lead electrocardiograms", Postgrad Med J 2005;81:122-125. doi: 10.1136/pgmj.2004.021204, submitted Feb. 27, 2004, accepted Mar. 29, 2004.

Welinder, "Differences in QRS Axis Measurements, Classification of Inferior Myocardial Infarction, and Noise Tolerance for 12-Lead Electrocardiograms Acquired From Monitoring Electrode Positions Compared to Standard Locations", Am J Cardiol 2010;106:581-586, accepted Mar. 28, 2010.

* cited by examiner

WEARABLE FOR ACQUISITION OF RESTING MULTI-LEAD ECG

STATEMENT REGARDING FEDERALLY-SPONSORED RESEARCH OR DEVELOPMENT

The U.S. Government has a paid-up license in this invention and the right in limited circumstances to require the patent owner to license others on reasonable terms provided for by the terms of the Phase I grant number NNJ07JB19C and Phase II grant number NNC08CA75C awarded by the National Aeronautics and Space Administration.

BACKGROUND OF THE INVENTION (1) Field of the Invention

The present invention relates to an electrode wearable and more particularly to an electrode wearable suitable for the acquisition of multi-lead ECG including 12-or-more-lead ECG with various features that enhance the use and performance of the electrode wearable. The present invention further relates to a method of taking biopotential measurements.

(2) Description of Related Art

An accepted standard in electrocardiogram (ECG) recordings of subjects is the "12-lead" ECG, or in pediatric subjects or in certain adults undergoing specialized testing, the "13-, 14-, or 15-lead" ECG. In the context of this disclosure and in the ECG field generally, "lead" refers to a voltage difference between two electrodes or between an electrode and a "central terminal" such as Wilson's, rather than to a lead wire or its corresponding electrode. Thus a traditional 12-lead ECG does not actually require 12 electrodes (or 12 lead wires), but usually only 10 electrodes: six standard "precordial" electrodes placed on the chest (termed, from left to right across the chest, $V_1$, $V_2$, $V_3$, $V_4$, $V_5$, and $V_6$) and four standard "limb" electrodes placed on or near each of the four appendages (termed RA, LA, RL, and LL, for the right and left arms and legs, respectively). Similarly, a common type of pediatric ECG uses all of the above electrodes but also adds so-called $V_{3R}$ and/or $V_{4R}$ electrodes (directed more rightward) and/or a $V_7$ electrode (directed more extremely to the left and approaching the back). While the traditional placement of the appendage electrodes is distally, as far as possible away from the heart, modified electrode placement schemes which have relocated the distal electrodes to proximal positions on the torso have also gained clinical acceptance, e.g., the Mason-Likar placement. Another modified electrode placement known as the Lund placement system has been shown to yield measurements that are in better agreement with the traditional distal ECG electrode placement scheme than those measurements recorded with the Mason-Likar method (see, e.g., Welinder et al., "Differences in QRS Axis Measurements, Classification of Inferior Myocardial Infarction, and Noise Tolerance for 12-Lead Electrocardiograms Acquired From Monitoring Electrode Positions Compared to Standard Locations", *Am J Cardiol* 2010;106:581-586).

A traditional ECG setup requires extensive time, training and expertise to set up and record high-quality signals suitable for analysis and/or diagnosis of disease or defect. Conventional gel-type electrodes require skin preparation at the electrode sites involving cleaning and abrasion to remove dead skin cells at the epidermis that increase electrode impedance and lower signal quality. Electrodes themselves must be properly cleaned and gelled prior to use, or pre-fabricated disposable electrodes must be used, which contribute to cost. Electrodes must be placed at the proper sites on the skin and not misplaced at sites too distant from clinically accepted placements, otherwise, the variability of placements can result in incomparable recordings which can increase the complexity of analysis and result in misdiagnosis (see, e.g., Jowett et al., "Modified electrode placement must be recorded when performing 12-lead electrocardiograms," *Postgrad Med J* 2005;81:122-125). Lead wires must be kept trim and orderly, so as to reduce motion artifact and noise and eliminate the possibility of accidental dislocation, and care must be taken to connect lead wires correctly at both ends, so as not to produce a faulty recording. Altogether, the knowledge, patience, and care that must be taken to record quality ECG recordings using traditional equipment and methods is beyond that possessed by the average ECG subject, making self-administration impractical, and rapid administration impossible even with the assistance of an expert technician or clinician to aid in the recording setup.

Various wearables have been developed to solve some of the above problems. U.S. Pat. No. 4,608,987 to Miller depicts a vest to which lead wires attach externally on the chest. U.S. Design Pat. No. 313,652 to Lavine illustrates a vest with electrodes and lead wires embedded in it, along with "arms" of unascertainable function. U.S. Pat. No. 5,224,479 teaches a 12-lead ECG diagnostic pad with belts for attachment at the shoulders. U.S. Pat. Nos. 6,205,346 and 6,341,229 to Akiva describe an apron holding ECG and other sensors; the device of the former disclosure requires bracelets. U.S. Pat. No. 6,408,200 to Takashina shows an electrode-embedded apron which can be placed over a supine subject. U.S. Pat. No. 6,516,289 to David teaches a glove or glove-and-sling apparatus which requires the subject to hold his left arm across his chest. U.S. patent application Ser. No. 10/937,539 of Wolff et al. briefly discusses a form-fitting sensor harness applied by means of an adhesive backing. U.S. Pat. No. 7,266,405 to Alroy et al. teaches a foldable electrode assembly designed to be portable and easily used by the unaided subject. U.S. patent application Ser. No. 11/713,334 shows a harness that aids in electrode placement on the chest. U.S. patent application Ser. No. 11/576,765 of Montplaisir shows a system of three straps, one for the chest and one for each arm. U.S. patent application Ser. No. 11/719, 338 of Gazit and Ser. No. 11/749,253 of Kurzweil et al. describe belt-type electrode harnesses with straps. U.S. patent application Ser. No. 12/464,878 of Grossman describes an ECG shirt comprising a elastic shirt having holes at various sites for electrode placement and elastic straps for fastening electrodes and lead wires, and having printed upon the shirt various labels and instructions to aid in placement or for training purposes. The teachings of all of the foregoing publications are expressly incorporated by references; many of the foregoing publications further list other references, each of which is also herein incorporated by reference.

Despite all the various contemplations by others, not all of the problems of quickly and accurately acquiring a resting 12-or-more-lead ECG have been solved by existing designs. Many of the designs use proximal electrode placements of the limb electrodes, whereas more distal placement is preferable; those that use more distal placement resort to additional apparatus (such as bracelets, belts, or gloves, or adhesives) or disadvantageous methods of use (such as requiring the subject to forcefully squeeze his or her arms against his or her chest or against electrodes placed in or near the armpits) in order to record signals from more distal electrode sites. Many of the designs require gels or adhesives to be placed on the body, which can dry out, become uncomfortable, and result in poor recordings because of increased electrode impedance or failure of electrode attachment. Many of the previous devices are susceptible to myoelectric noise or are uncomfortable to wear, even for short periods, although ideally an apparatus for collecting resting multi-lead ECG is comfortable to wear over a period of several minutes or longer. Many of them are too complicated to be donned or doffed unaided. Many of them involve excessive pieces or components which are less conveniently stored or transported.

In view of the foregoing drawbacks, it is an object of the present invention to provide a electrode wearable for resting multi-lead ECG, including for 12-or-more-lead ECG, that comes in one piece and preferably has no more than one point of connection/disconnection around the body, so that it can be easily, quickly, and comfortably donned and resized, providing the proper electrode placement without possibility of incorrect placement, without the use of adhesives on the body, and without requiring substantial muscular exertion on the part of the subject during ECG recording which can taint the ECG signal with myoelectric noise. It is further the object of the present invention to provide an electrode wearable than can be used and re-used without cleaning or preparation of electrodes or skin sites so as to provide an "always-ready, instant-on" electrode wearable. It is further the object of the present invention to provide an electrode harness or vest which records the appropriate limb electrode signals from placement sites that are more distal than those of other electrode harnesses and vests without requiring a multiple-piece apparatus that may be susceptible to misplacement or misuse by the untrained individual and in any case would require additional time and hassle to don and doff. Finally, it is the object of the present invention to have an electrode wearable containing dry electrodes.

SUMMARY OF THE INVENTION

The present invention relates to an electrode wearable and more particularly to an electrode harness with various features, which enhance the use and performance of the electrode harness. The present invention further relates to a method of taking biopotential measurements.

Various occupations and missions, including those of exploratory, military and astronautical nature, preclude access to diagnostic medical aid by trained professionals and traditional diagnostic equipment and procedures. In such cases, it is critical for workers and crewmembers to be able to monitor their own or their colleagues' health statuses and make decisions based on feedback from biomedical monitoring systems. These systems must be simplified for rapid donning and doffing, automatic checkout capability, annunciation and guidance, and ensuring the health and safety of each worker or crewmember. The sensors that are used for biomedical monitoring therefore should preferably be low profile, accurate, reliable, and with as few wires as possible. In such scenarios, the use of electrodes with electrode gel and overtaps has not been highly successful, resulting in skin irritation, adhesion problems, stowage concerns and limited life/inventory issues. Furthermore, as commonality between and among systems is highly beneficial, biomedical sensors used for one type of monitoring should preferably be simple and interchangeable for other types of monitoring. Even in scenarios where professional care may be more available/accessible, it may still be convenient to have an easily stowed, readily used physiological data acquisition system on hand.

The padded harnesses of the type described in this disclosure overcome the significant problem of tenting associated with other electrode harnesses and wearables, and particularly with tight-fitting elastic-fabric shirt-type electrode wearables and belt-type electrode wearables. A common though unsatisfactory solution to electrode harness problems is simply to provide a tight-fitting elastic shirt or an adjustable belt and embed it with electrodes at the desired electrode sites. However, the inventors' experimentation with such apparatus has shown that because the anatomical structure of the body, and particularly the chest, is not uniformly convex, protrusions on the body (as at the pectorals or breasts) create concavities (as at the sternum) where electrode contact is poor or nonexistent, because of the poor or nonexistent inward pressure exerted by portions of the wearable tented between two convex portions of the body. Whereas an object of the present invention is to provide a wearable which can be used and applied to numerous individuals without laborious personal customization, the padded electrode wearables and harnesses described here overcome these significant drawbacks which make previously described apparatus of limited or no practical use for many subjects and body types.

While the electrode harness and methods of the present invention allow for use with most applications where biopotential measurements are taken, and may be adapted to accommodate many different sensor placement configurations as well as all manner of sensors, the particular wearable of the present invention is suitable for collection of resting 12-lead ECGs, or when desired resting 13-, 14-, 15- or more-lead ECGs, although the total number of electrodes used may be less than the standard ten (e.g., for 12-or-more-lead ECGs derived from lesser, non-standard numbers of electrodes), or more than the maximum number electrodes depicted on any drawing herein. The electrode harness is further preferably part of a system, which includes either wireless or tethered bridges between the electrode harness and a recorder/monitor, or has the recorder/monitor integrated within it, and preferably includes various forms of processors for analyzing the biopotential signal.

The electrodes used with the electrode harness and methods of the present invention may include but are not limited to gel-type electrodes and dry electrodes. The gel-type electrodes usually comprise a sensing element and a conductive gel for transmitting the signal between the subject's skin and the sensing element. Preferably, however, dry electrodes are used. The dry electrodes comprise a penetrator for detecting physiological signals below the surface of the skin as a sensing element. Dry physiological recording electrodes of the type described in U.S. Pat. No. 6,782,283 are herein incorporated by reference. Dry electrodes provide the advantages that there is no gel to dry out, no need to abrade or clean the skin, and the electrode may be applied in hairy areas such as an adult male human's chest is likely to be. Alternatively, the subject's skin may be mechanically abraded, or an amplified electrode may be used. Preferably, at least two electrodes are used, one a signal electrode and the other a reference electrode. The at least two electrodes do not have to be of the same type, that is, for example, one could be a conductive gel electrode and the other a dry electrode. The at least two electrodes can be any shape known to be useful to those skilled in the art. For example, the electrodes can be circular or non-circular in shape. The term "dry electrode" as used in this disclosure shall expressly refer, unless otherwise indicated, to the dry penetrating electrode of U.S. Pat. No. 6,782,283 or dry electrode of similar design and functionality, and shall expressly not merely be a conventional electrode that has not been gelled, a conductive plate which does not solve the problem of increased surface skin impedance, a capacitive or optical sensor, or an active sensor which does not otherwise have the properties of the U.S. Pat. No. 6,782,283 dry electrode.

Alternatively or in addition, textile electrodes of the type described in U.S. Pat. No. 7,308,294 to Hassonjee et al. or U.S. patent application Ser. No. 12/670,455 of Niemi et al. or similar may be used. Both of these disclosures are fully incorporated by reference herein. Textile electrodes have the advantages that they are flexible and light and washable along with the wearable. Their full integration into the garment may be a disadvantage, however, in the event of electrode failure, as the inability to easily swap out a faulty electrode means that the whole garment must be replaced and thus that full extra garments must be stored and transported rather than just extra swappable electrodes.

The electrode wearable of the present invention may take the form of a harness, bra, belt, strap, vest, jacket, shirt, tubular top, bodysuit, coverall, lifejacket, or other such wearable known in the art. Preferably, electrode wearable is a harness supported by at least one shoulder strap slung high on the shoulder near to the neck so as not to be susceptible to slipping off, as straps located near the edge of the shoulder(s) can be. Where the word "harness" is used throughout this disclosure, any of the other various forms listed above are included, as it is supposed that a person skilled in the art would be capable of adapting the features described to the other various forms.

The electrode harness of the present invention overcomes one or more of the significant drawbacks of other electrode systems. One of the features of various embodiments of the present invention is a single-piece design. Not having multiple pieces to don, fit, adjust, or correctly place eliminates any opportunity to misapply the device or have pieces of the device become separated from each other, reduces setup time, and simplifies setup. Another of the features of various embodiments of the present invention is no more than a single point of connection/disconnection around the body. This prevents clutter, prevents the possibility of separation of the electrode wearable into multiple pieces which could become separated and misplaced, and reduces as much as possible the amount of time required to don and doff the electrode wearable. Preferably, the connection point is easily and readily resizable so as to enable the wearer to self-adjust the harness to a perfect snug fit around the body, either before donning, or during wear, or during the process of donning. Another feature of various embodiments of the present invention is the use of dry electrodes (as described earlier in this disclosure) which are reusable, reliable, and provide quality signals without the need for electrode or skin cleaning or preparation. The use of dry penetrating electrodes drives and enables the usefulness of the described embodiments as always-ready, instant-on, instant-off, reusable-anytime appliances. Without the enabling use of such dry electrodes, the embodiments as intended to be used would be difficult to conceive or realize, since as practical matters they would require electrode/skin preparation or the use of one-time-only use electrodes which would unacceptably increase setup time, add to the cost of consumables, etc. Another feature of various embodiments of the present invention is the use of no adhesives. Adhesives are often used in such systems to stick electrodes to the skin, both fixing the site of the electrode placement and providing the leverage needed for the electrode to be pressed against the skin surface so as to make good electrical contact. Besides contributing to setup time and complexity, adhesives can become uncomfortable and frequently leave the skin undesirably sticky after use. Yet another feature of various embodiments of the present invention is the use of pads or pillows on the sides of the harness, underneath the arms, which permit for more distal arm electrode placement and supply the needed pressure to press the arm electrodes up against the arms while the arms are comfortably at rest, without requiring the subject to squeeze his or her arms down or against electrodes or muscularly exert the arms in any way, and without requiring the subject to wear additional electrodes on bracelets, gloves, or arm bands, and without needing adhesives to stick electrodes to the arms. Still another feature of various embodiments of the present invention is the use of padding over the sternum for pushing certain precordial electrodes on or near the sternum (e.g., $V_1$, $V_2$, $V_3$ and $V_3R$ electrodes, whenever individually or collectively present) down toward the chest. The sternum being a cavity, there is a tendency for dry electrodes or textile electrodes to tent, resulting in poor abutting of electrodes on the chest, thus increasing electrode impedance or severing the electrode/skin electrical connection altogether. The additional padding eliminates tenting over the sternum and brings the aforementioned electrodes into good electrical contact with their respective sites.

In one embodiment, the present invention includes a wearable for administration or self-administration of a resting multi-lead ECG, including a 12-or-more-lead ECG from full or reduced electrode sets, of a subject having arms, the wearable comprising a thin flexible electrode support supporting a plurality of electrodes, including at least one precordial electrode but preferably at least six (e.g., $V_1$, $V_2$, $V_3$, $V_4$, $V_5$, $V_6$) or optionally more (e.g., add $V_3R$ and/or $V_4R$ and/or V7) precordial electrodes and the LA, RA and LL electrodes and preferably also a ground ("RL") electrode, and electrode-supporting cushions attached to or integral to the electrode support, placed on the electrode support such that pressure is exerted by the cushions upon arms directed downwardly in either the sideward, backward or forward direction, the pressure being sufficient to make cushion-mounted LA and RA electrodes contact with the medial, posterior or anterior surfaces of the arms without substantial muscular exertion on the part of the subject to press the arms into the cushion-mounted LA and RA electrodes. In this embodiment, pressure is exerted on the cushions by the downward force of the subject's resting arms in either the sideward, backward or forward direction, this pressure being produced by natural biomechanical or gravitational forces and being sufficient to allow cushion-mounted LA and RA electrodes to electrically contact the medial, posterior or anterior surfaces of the arms without requiring substantial muscular exertion on the part of the subject (meaning any exertion that is not easily sustainable over a period of several hours). The thin flexible electrode support can be made of any type of textile or material known in the art, for example, Schoeller Textile 15267. The electrodes may be permanently affixed or embedded in the thin flexible electrode support, or may be attached thereto by means of mechanical or electrical connectors. The mechanical or electrical connectors by which the electrodes are fastened to or integrated with the electrode support can be releasable, lockable, non-releasable or permanent connections as described in U.S. patent application Ser. No. 10/988,358 which is herein incorporated by reference. The electrode-supporting cushions may be padded or inflatable or may provide the requisite cushioning by any means known in the art. Inflatable/deflatable cushions permit the wearable to be more collapsible for storage or transport, whereas padding cushioning may provide padding for the more sensitive or fragile parts of the wearable (such as embedded electronics) when folded or rolled up and tucked away for storage or transport. Suitable padding for the cushions may be of any material known in the art, including, for example, polyurethane open cell foam or reticulated foam. Preferably, the arms are completely at rest and allowed to effortlessly abut with the cushions and their electrodes. The electrodes may be of any type known in the art, but are preferably dry electrodes as described in this disclosure. Preferably, the wearable comprises at least one shoulder strap. Preferably, the shoulder strap is adjustable. Further preferably, the shoulder strap is adjustable without being capable of coming completely undone. Preferably the wearable is fastened about the torso by no more than a single point of connection/disconnection about the body. The point of connection/disconnection can be any fastener known in the art, such as a hook, button, snap, zipper, clasp, clip or clip mechanism, buckle, or hook-and-loop material (VELCRO or similar). The point of connection/disconnection around the body, if present, is preferably adjustable so as to resize/tighten the wearable to provide a snug fit. Preferably, the fastener is an elongated hook as illustrated in the drawings. The adjustability may be by means of any type of buckle or scheme known in the art. One example of a type of adjustability scheme which is adjusted at the time of donning would be a hook that mates to one of a multiplicity of loops spaced apart from each other such that the appropriate loop may be selected at the time of donning to provide the snuggest comfortable fit. A person skilled in the art would appreciate that a similar fastening scheme could be conceived with a single loop and multiple hooks, with a single button and multiple buttonholes, a single buttonhole and multiple buttons, a single zipper-half on one side and multiple zipper-halves on the other, a single male snap and multiple female snaps on the other or vice versa, multiples of either type of the above fasteners on either side, and other such variants on the concept, without departing from the "single point of connection/disconnection" described elsewhere in this disclosure. What is meant by "a single point of connection/disconnection" is that there need not be fastened or adjusted multiple belts or straps, or a single belt or strap may not be unfastened in more than one place: preferably, the wearer (or assistant) should need only make a mechanical disconnection at a single point or area in order to free the user from the wearable. This limitation should not foreclose the possibility of the single point of connection being fastened by, for example, multiple parallel hooks. What is key to "a single point of connection/disconnection" is that it can be advantageously done or undone with a single manual operation, unlike multiple belt buckles or a series of buttons.

In a variation of the above embodiment, the wearable comprises RA and LA electrodes placed on the lateral surfaces of the electrode-supporting cushions that naturally abut and make good electrical contact with the medial surfaces of the arms.

In a different variation of the above embodiment, the wearable comprises RA and LA electrodes placed on the anterior surfaces of the electrode-supporting cushions that naturally abut and make good electrical contact with the posterior surfaces of the arms.

In a different variation of the above embodiment, the wearable comprises RA and LA electrodes placed on the posterior surfaces of the electrode-supporting cushions that naturally abut and make good electrical contact with the anterior surfaces of the arms.

Other variations of the first embodiment incorporate multiple of the above-mentioned sets of cushion-mounted RA and LA electrodes such that RA and LA electrodes naturally abut and make good electrical contact with the medial or posterior, medial or anterior, posterior or anterior, or medial, posteror, or anterior surfaces of the arms depending upon the placement of the arms.

In another embodiment, the present invention includes a wearable for administration or self-administration of a resting 12-or-more-lead ECG of a subject having a chest having a sternum, the wearable comprising a thin flexible electrode support supporting a plurality of electrodes, including at least one precordial electrode but preferably at least six (e.g., $V_1$, $V_2$, $V_3$, $V_4$, $V_5$, $V_6$) or optionally more (e.g., add $V_3R$ and/or $V_4R$ and/or V7) precordial electrodes and LA, LL and RA electrodes and a preferably also a ground ("RL") electrode, each electrode having a respective placement site, the thin flexible electrode support comprising padding over the sternum such that any electrodes subject to tenting over the sternum, including $V_1$, $V_2$, $V_3$ and $V_{3R}$, whenever individually or collectively present, are pushed down toward the chest, bringing them into good electrical contact with their respective sites. The padding may be of any type known or described previously, and must operate to prevent the tenting of the electrodes over the sternum cavity. As an alternative to or in addition to padding, the electrode support may be inflatable so as to achieve the same effect as or augment the effect of padding.

In another embodiment, the present invention includes a single-piece wearable for administration or self-administration of a resting 12-or-more-lead ECG of a subject, the single-piece wearable comprising a thin flexible electrode support supporting a plurality of electrodes, including at least one precordial electrode but preferably at least six (e.g., $V_1$, $V_2$, $V_3$, $V_4$, $V_5$, $V_6$) or optionally more (e.g., adding $V_{3R}$ and/or $V_{4R}$ and/or V7) precordial electrodes, and LA, RA, and LL electrodes and a preferably also a ground ("RL") electrode, the LA and RA electrodes disposed to contact with preferably the medial, posterior or anterior aspect of the arms, without the use of any adhesive on the subject's body, without additional belts, bands, gloves, or bracelets other than what is provided in the thin flexible electrode support, wherein the thin flexible electrode support has no more than one point of connection/disconnection around the body. As described previously, the point of connection/disconnection can be any fastener known in the art, such as a hook, button, snap, zipper, clasp, clip or clip mechanism, buckle, or hook-and-loop material (VELCRO or similar). The point of connection/disconnection around the body, if present, is preferably adjustable so as to resize/tighten the wearable to provide a snug fit. Key to this embodiment is the lack of multiple pieces to the apparatus, such as bands that might go around the arms.

In yet another embodiment, the present invention consists of a method of acquiring biopotential measurements comprising a subject having arms donning a padded or inflated electrode wearable having a plurality of electrodes, each electrode having a corresponding electrode placement site on the subject including RA, LA, and LL, and the wearable having sufficient padding or inflation in a thin flexible electrode support to press the wearable's electrodes into the surface of the subject's skin on all electrode sites and to prevent tenting of electrodes, and the wearable having electrode-supporting cushions of sufficient padding or inflation to press RA and/or LA electrodes mounted on the lateral, anterior, and/or posterior surfaces of the cushions into the medial, posterior, and/or anterior surfaces of the subject's arms, wherein the donning is performed by wrapping the thin flexible electrode support about the torso of the subject, adjusting the size or tightness of the thin flexible electrode support, and, after or before adjusting the size or tightness, connecting the two ends of the thin flexible electrode support together at only a single point of connection; tucking the LL electrode enclosed by the thin flexible electrode support into a lower garment worn by the subject; the subject sitting, standing or supine; the subject relaxing the arms, the medial, posterior and/or anterior surfaces of the arms making good contact with the RA and LA electrodes, and the cushions providing sufficient pressure of the RA and LA electrodes against the arms; and acquiring or measuring biopotentials of the subject via the wearable's electrodes. Preferably, the acquired or measured biopotentials are transmitted wired or wirelessly for recording and/or viewing. Preferably, the biopotential measurements acquired comprise a resting 12-or-more-lead ECG. The lower garment of the subject can be a belt, pants, underpants, panties, hosiery, skirt, or similar. Preferably, the RA and LA electrodes are mounted on the superior lateral, superior anterior, and/or superior posterior surfaces of the cushions.

In a variation of the above embodiment, the method comprises the donning of a wearable having electrode-supporting cushions of sufficient padding or inflation to press RA and/or LA electrodes mounted on the lateral surfaces of the cushions into the medial surfaces of the subject's arms, the medial surfaces of the arms making good contact with the RA and LA electrodes. In this embodiment, the arms are preferably relaxed to the sides of the subject's body.

In another variation of the above embodiment, the method comprises the donning of a wearable having electrode-supporting cushions of sufficient padding or inflation to press RA and/or LA electrodes mounted on the anterior surfaces of the cushions into the posterior surfaces of the subject's arms, the posterior surfaces of the arms making good contact with the RA and LA electrodes. In this embodiment, the arms are preferably relaxed to the front of the sides of the subject's body.

In yet another variation of the above embodiment, the method comprises the donning of a wearable having electrode-supporting cushions of sufficient padding or inflation to press RA and/or LA electrodes mounted on the posterior surfaces of the cushions into the anterior surfaces of the subject's arms, the anterior surfaces of the arms making good contact with the RA and LA electrodes. In this embodiment, the arms are preferably relaxed to the back of the sides of the subject's body.

Other variations of the above embodiment incorporate into the wearable multiple of the above-mentioned sets of cushion-mounted RA and LA electrodes such that RA and LA electrodes naturally abut and make good electrical contact with the medial or posterior, medial or anterior, posterior or anterior, or medial, posteror, or anterior surfaces of the arms depending upon the placement of the arms.

In yet another embodiment, the present invention consists of a method of acquiring biopotential measurements comprising a subject having arms donning a padded or inflated electrode wearable having a plurality of electrodes each having a corresponding electrode placement site on the subject including RA, LA, and LL sites and the wearable having sufficient padding or inflation in a thin flexible electrode support to press the wearable's electrodes into the surface of the subject's skin on all electrode sites and to prevent tenting of electrodes and the wearable having electrode-supporting cushions of sufficient padding or inflation to press RA and LA electrodes mounted on the lateral surfaces of the cushions into the medial surfaces of the subject's arms, wherein the donning is performed by wrapping the thin flexible electrode support about the torso of the subject, adjusting the size or tightness of the thin flexible electrode support, and, after or before adjusting the size or tightness, connecting the two ends of the thin flexible electrode support together at only a single point of connection; tucking the LL electrode enclosed by the thin flexible electrode support into a lower garment worn by the subject; the subject laying supine; the subject relaxing the arms, the medial surfaces of the arms making good contact with the RA and LA electrodes, and the cushions providing sufficient pressure of the RA and LA electrodes against the arms; and acquiring or measuring biopotentials of the subject via the wearable's electrodes. Preferably, the acquired or measured biopotentials are transmitted wired or wirelessly for recording and/or viewing. Preferably, the biopotential measurements acquired comprise a resting 12-lead ECG. The lower garment of the subject can be a belt, pants, underpants, panties, hosiery, skirt, or similar. Preferably, the RA and LA electrodes are mounted on the superior lateral surfaces of the cushions.

In yet another embodiment, the present invention consists of a method of acquiring biopotential measurements comprising a subject having arms donning a padded or inflated electrode wearable having a plurality of electrodes each having a corresponding electrode placement site on the subject including RA, LA, and LL sites, and the wearable having sufficient padding or inflation in a thin flexible electrode support to press the wearable's electrodes into the surface of the subject's skin on all electrode sites and to prevent tenting of electrodes and the wearable having electrode-supporting cushions of sufficient padding or inflation to press RA and LA electrodes mounted on the anterior surfaces of the cushions into the posterior surfaces of the subject's arms, wherein the donning is performed by wrapping the thin flexible electrode support about the torso of the subject, adjusting the size or tightness of the thin flexible electrode support, and, after or before adjusting the size or tightness, connecting the two ends of the thin flexible electrode support together at only a single point of connection; tucking the LL electrode enclosed by the thin flexible electrode support into a lower garment worn by the subject; the subject laying supine; the subject relaxing the arms on tops of the cushions, the posterior surfaces of the arms making good contact with the RA and LA electrodes, and the cushions providing sufficient pressure of the RA and LA electrodes against the arms; and acquiring or measuring biopotentials of the subject via the wearable's electrodes. Preferably, the acquired or measured biopotentials are transmitted wired or wirelessly for recording and/or viewing. Preferably, the biopotential measurements acquired comprise a resting 12-lead ECG. The lower garment of the subject can be a belt, pants, underpants, panties, hosiery, skirt, or similar. Preferably, the RA and LA electrodes are mounted on the superior anterior surfaces of the cushions.

In still another embodiment, the present invention consists of a method of acquiring biopotential measurements comprising a subject having arms donning a padded or inflated electrode wearable having a plurality of electrodes including an LL electrode, a first RA electrode, a second RA electrode, a first LA electrode, and a second LA electrode, each electrode having a corresponding electrode site on the subject, and the wearable having sufficient padding or inflation in a thin flexible electrode support to press the wearable's electrodes into the surface of the subject's skin on all electrode sites and to prevent tenting of electrodes and the wearable having electrode-supporting cushions of sufficient padding or inflation to press first RA and LA electrodes mounted on the anterior surfaces of the cushions into the posterior surfaces of the subject's arms and second RA and LA electrodes mounted on the lateral surfaces of the cushions into the medial surfaces of the subject's arms, wherein the donning is performed by wrapping the thin flexible electrode support about the torso of the subject, adjusting the size or tightness of the thin flexible electrode support, and, after or before adjusting the size or tightness, connecting the two ends of the thin flexible electrode support together at only a single point of connection; tucking the LL electrode enclosed by the thin flexible electrode support into a lower garment worn by the subject; the subject standing, sitting, or laying supine; the subject relaxing the arms, either the medial surfaces of the arms making good contact with the first RA and LA electrodes or the posterior surfaces of the arms making good contact with the second RA and LA electrodes, and the cushions providing sufficient pressure of the first or second RA and LA electrodes against the arms; automatically determining whether the arms are making contact with the first or second set of RA and LA electrodes by checking the impedance of the first and second sets of RA and LA electrodes; and acquiring or measuring biopotentials of the subject via the wearable's electrodes. Preferably, the acquired or measured biopotentials are transmitted wired or wirelessly for recording and/or viewing. Preferably, the biopotential measurements acquired comprise a resting 12-lead ECG. The lower garment of the subject can be a belt, pants, underpants, panties, hosiery, skirt, or similar. Preferably, the first RA and LA electrodes are mounted on the superior lateral surfaces of the cushions and the second RA and LA electrodes are mounted on the superior anterior surfaces of the cushions.

In still another embodiment, the present invention consists of a method of acquiring biopotential measurements comprising a subject having arms donning a padded or inflated electrode wearable having a plurality of electrodes including an LL electrode, a first RA electrode, a second RA electrode, a third RA electrode, a first LA electrode, a second LA electrode, and a third LA electrode, each electrode having a corresponding electrode site on the subject, and the wearable having sufficient padding or inflation in a thin flexible electrode support to press the wearable's electrodes into the surface of the subject's skin on all electrode sites and to prevent tenting of electrodes and the wearable having electrode-supporting cushions of sufficient padding or inflation to press first RA and LA electrodes mounted on the anterior surfaces of the cushions into the posterior surfaces of the subject's arms, second RA and LA electrodes mounted on the lateral surfaces of the cushions into the medial surfaces of the subject's arms, and third RA and LA electrodes mounted on the posterior surfaces of the cushions into the anterior surfaces of the subject's arms, wherein the donning is performed by wrapping the thin flexible electrode support about the torso of the subject, adjusting the size or tightness of the thin flexible electrode support, and, after or before adjusting the size or tightness, connecting the two ends of the thin flexible electrode support together at only a single point of connection; tucking the LL electrode enclosed by the thin flexible electrode support into a lower garment worn by the subject; the subject standing, sitting, or laying supine; the subject relaxing the arms, either the medial surfaces of the arms making good contact with the first RA and LA electrodes or the posterior surfaces of the arms making good contact with the second RA and LA electrodes or the anterior surfaces of the arms making good contact with the third RA and LA electrodes, and the cushions providing sufficient pressure of the first or second or third RA and LA electrodes against the arms; automatically determining whether the arms are making contact with the first or second or third set of RA and LA electrodes by checking the impedance of the first and second and third sets of RA and LA electrodes; and acquiring or measuring biopotentials of the subject via the wearable's electrodes. Preferably, the acquired or measured biopotentials are transmitted wired or wirelessly for recording and/or viewing. Preferably, the biopotential measurements acquired comprise a resting 12-or-more-lead ECG. The lower garment of the subject can be a belt, pants, underpants, panties, hosiery, skirt, or similar. Preferably, the first RA and LA electrodes are mounted on the superior lateral surfaces of the cushions, the second RA and LA electrodes are mounted on the superior anterior surfaces of the cushions, and the third RA and LA electrodes are mounted on the superior posterior surfaces of the cushions.

In still another embodiment, the present invention consists of a method of acquiring biopotential measurements comprising a subject having arms donning an electrode wearable having a plurality of electrodes including at least one alternate electrode for a given electrode placement site; testing the electrode-skin impedance of the at least one alternate electrode and the electrode for which it is an alternate; selecting the electrode determined to have the lower impedance in the previous step; and acquiring or measuring biopotentials of the subject via the wearable's electrodes including the selected electrode. Preferably, the biopotential measurements acquired comprise a resting 12-or-more-lead ECG.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DETAILED DESCRIPTION OF THE INVENTION

The present invention relates to an electrode harness and more particularly to an electrode harness with various features, which enhance the use and performance of the electrode harness. The present invention further relates to a method of taking a physiological or preferably a biopotential measurement.

Figure 7:
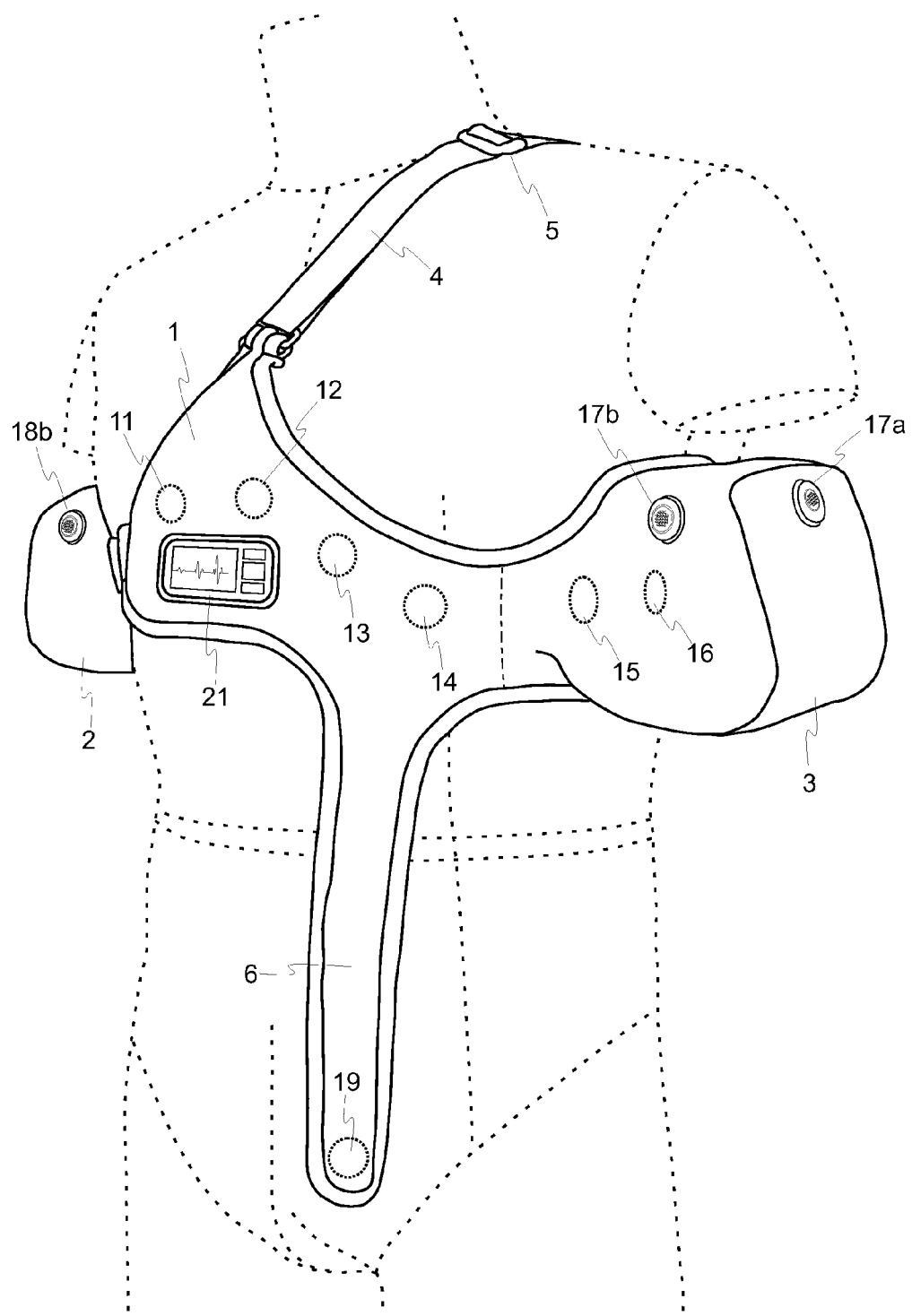
FIG. 7. Three-quarters left side perspective view of another embodiment of the present invention when worn, showing locations of electrodes.
Figure 9:
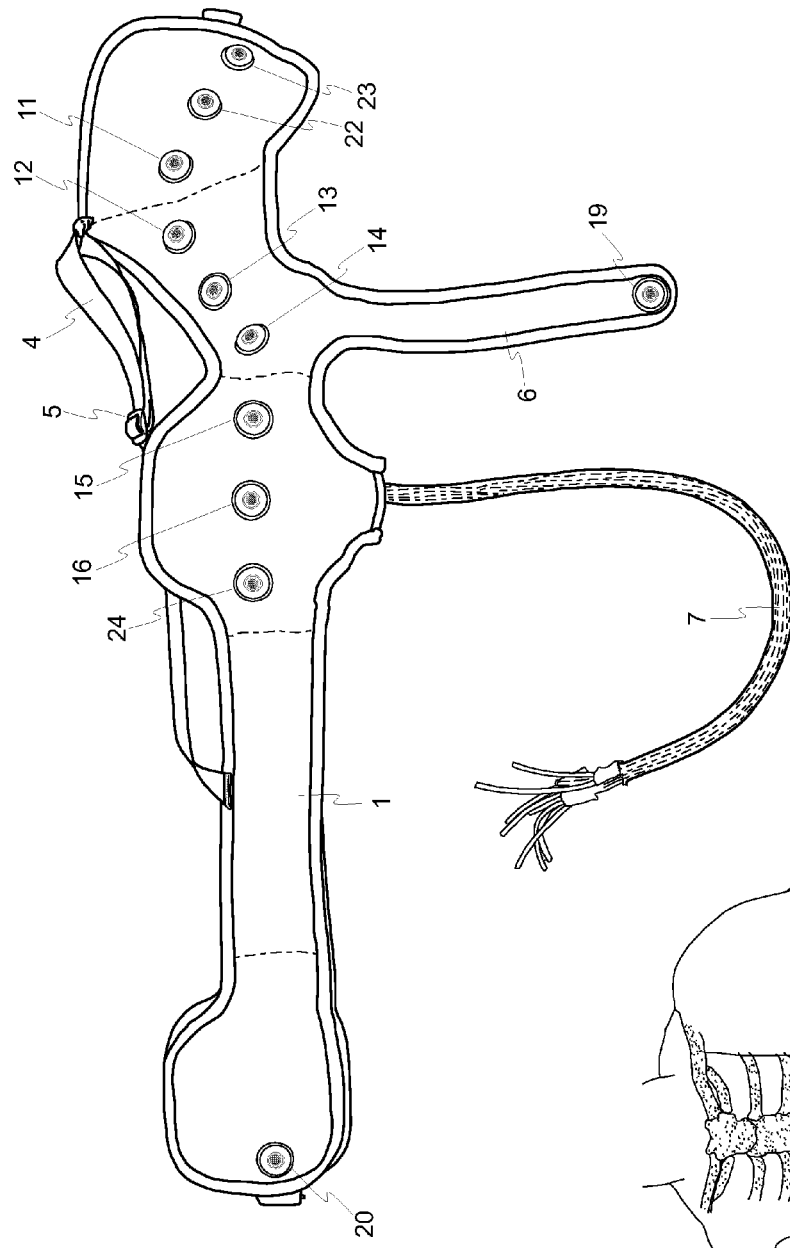
FIG. 9. Interior view of a pediatric or other specialized embodiment of the present invention when unfolded showing additional chest-abutting electrodes.

The drawings show different aspects of preferred embodiments of the invention. The figures largely show a single embodiment but with FIGS. 7 and 9 representing variations on that embodiment and thereby constituting different embodiments. It will be appreciated by a person skilled in the art that the features that distinguish the embodiments which are illustrated or described can be combined, expanded, multiplied and interchanged without departing from the spirit of the invention.

Figure 6:
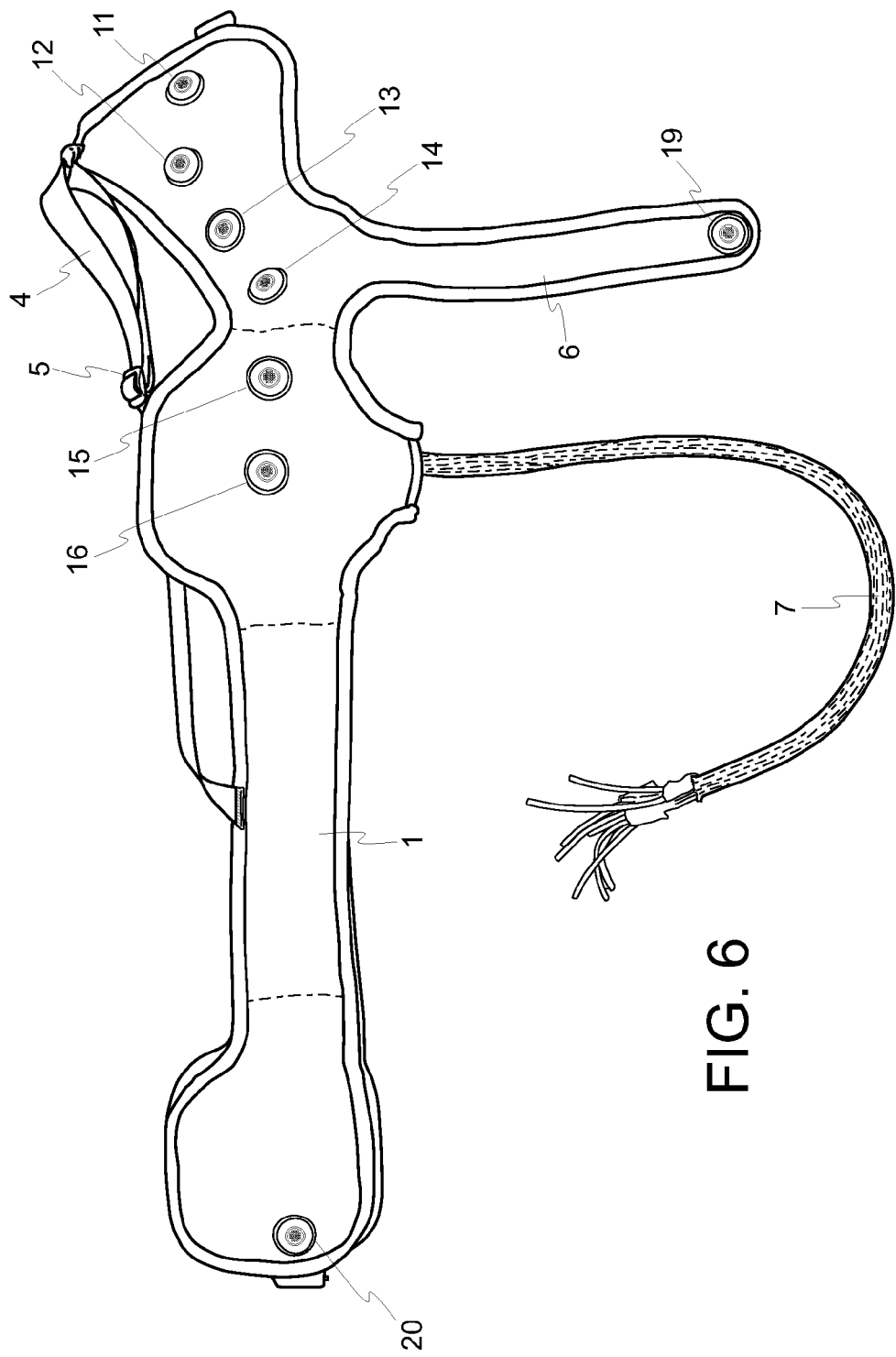
FIG. 6. Interior view of the same embodiment of the present invention when unfolded showing chest-abutting electrodes.

The electrode harness of the illustrated embodiment comprises a thin flexible electrode support 1 which supports a multiplicity of electrodes, including, according to their standard names known in the 12-lead ECG art, $V_1$ 11, $V_2$ 12, $V_3$ 13, $V_4$ 14, $V_5$ 15, and $V_6$ 16, placed roughly from left to right across the chest, and first LA electrode 17a for measurement at a medial site on the left arm, second LA electrode 17b for alternative measurement at a posterior site on the left arm, third LA electrode 17c for alternative measurement at an anterior site on the left arm, first RA electrode 18a for measurement at a medial site on the right arm, second RA electrode 18b for alternative measurement at a posterior site on the right arm, third RA electrode 18c for alternative measurement at an anterior site on the right arm, LL 19, and RL 20. As illustrated, a Lund or modified Lund electrode placement is used for the arm electrodes, and all electrodes are dry electrodes of the type described earlier in this disclosure. The electrode support 1 is capable of supporting electrodes of various sizes, and additional or fewer electrodes or electrodes in other arrangements. The electrode support 1 also comprises and encloses electrode lead wires (not shown) which are attached to the electrodes within the electrode support 1 with sufficient slack so as not to tug or pull on any of the electrodes as the harness is donned/doffed/repositioned or as the subject moves inside the harness. Alternately, instead of lead wires, electrical connections may be printed on various thin insulated layers internal to the electrode support 1. While in various circumstances any of the electrodes may serve as a reference or ground electrode, in common setups preferably RL electrode 20, as seen in FIG. 6, may serve as reference or ground.

The electrode support 1 can be fabricated of any thin flexible material known in the art, including Schoeller Textile 15267. As described earlier in this disclosure, the electrode support 1 is preferably padded both to optimize functionality and to prevent tenting of the electrodes. Alternatively, the electrode support may be inflated to provide the requisite pressure of the electrodes against the surface of the subject's skin.

Figure 1:
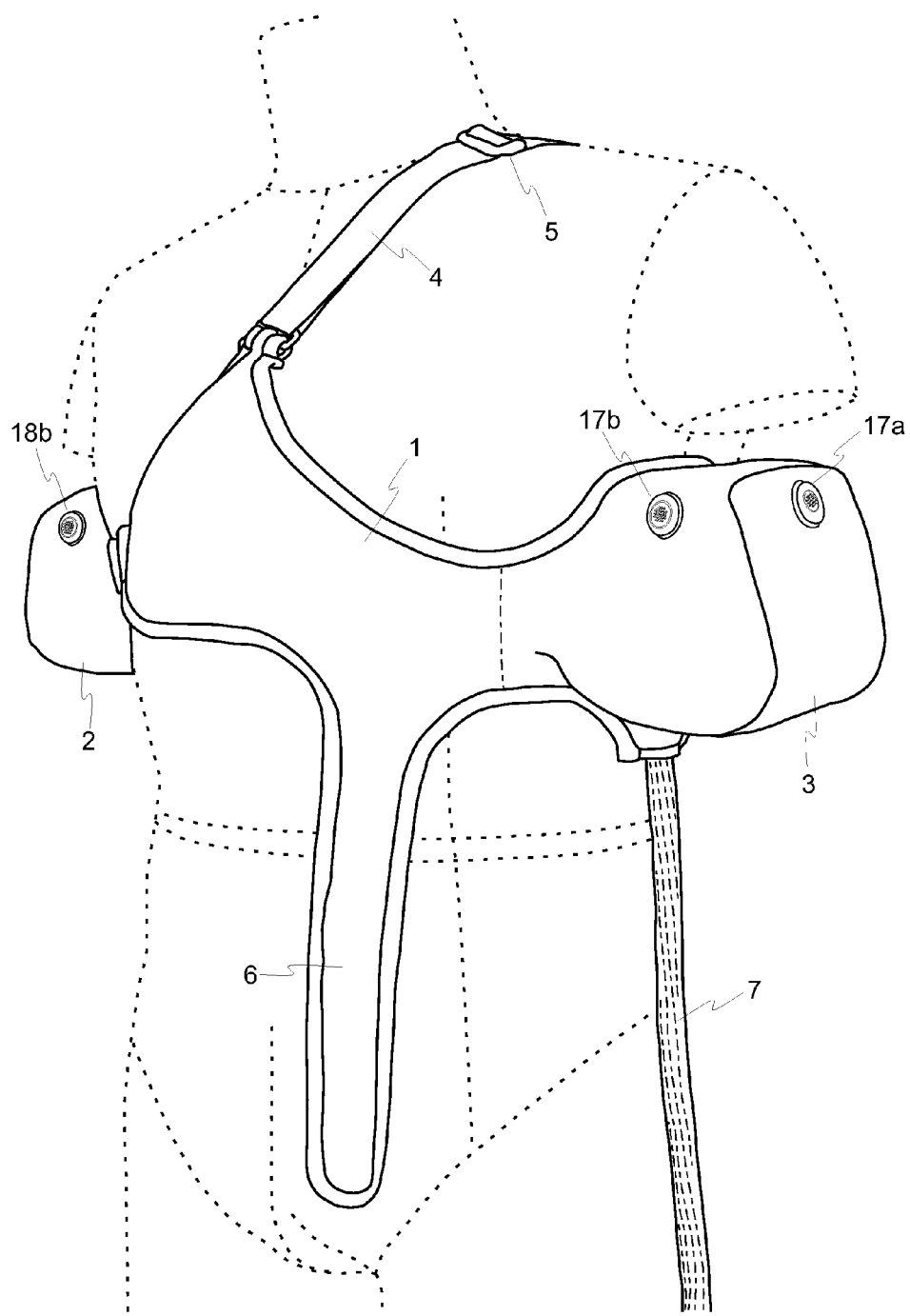
FIG. 1. Three-quarters left side perspective view of one embodiment of the present invention when worn.
Figure 2:
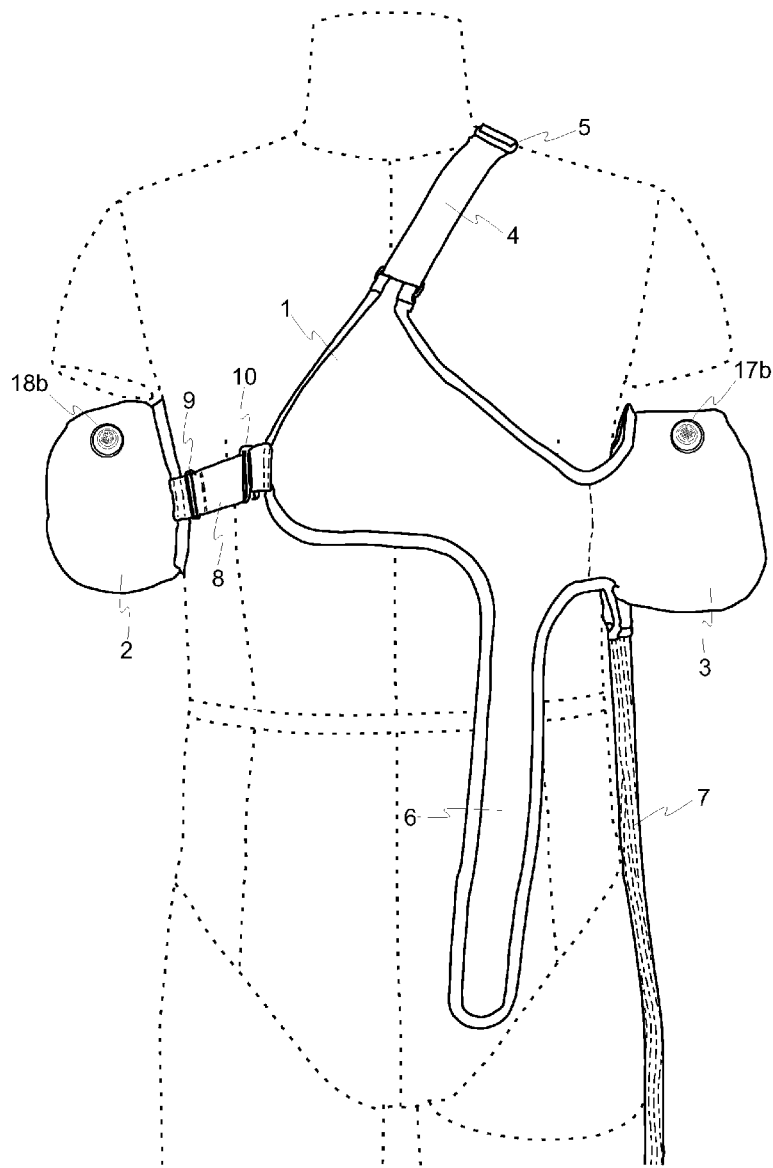
FIG. 2. Front perspective view of the same embodiment of the present invention when worn.
Figure 3:
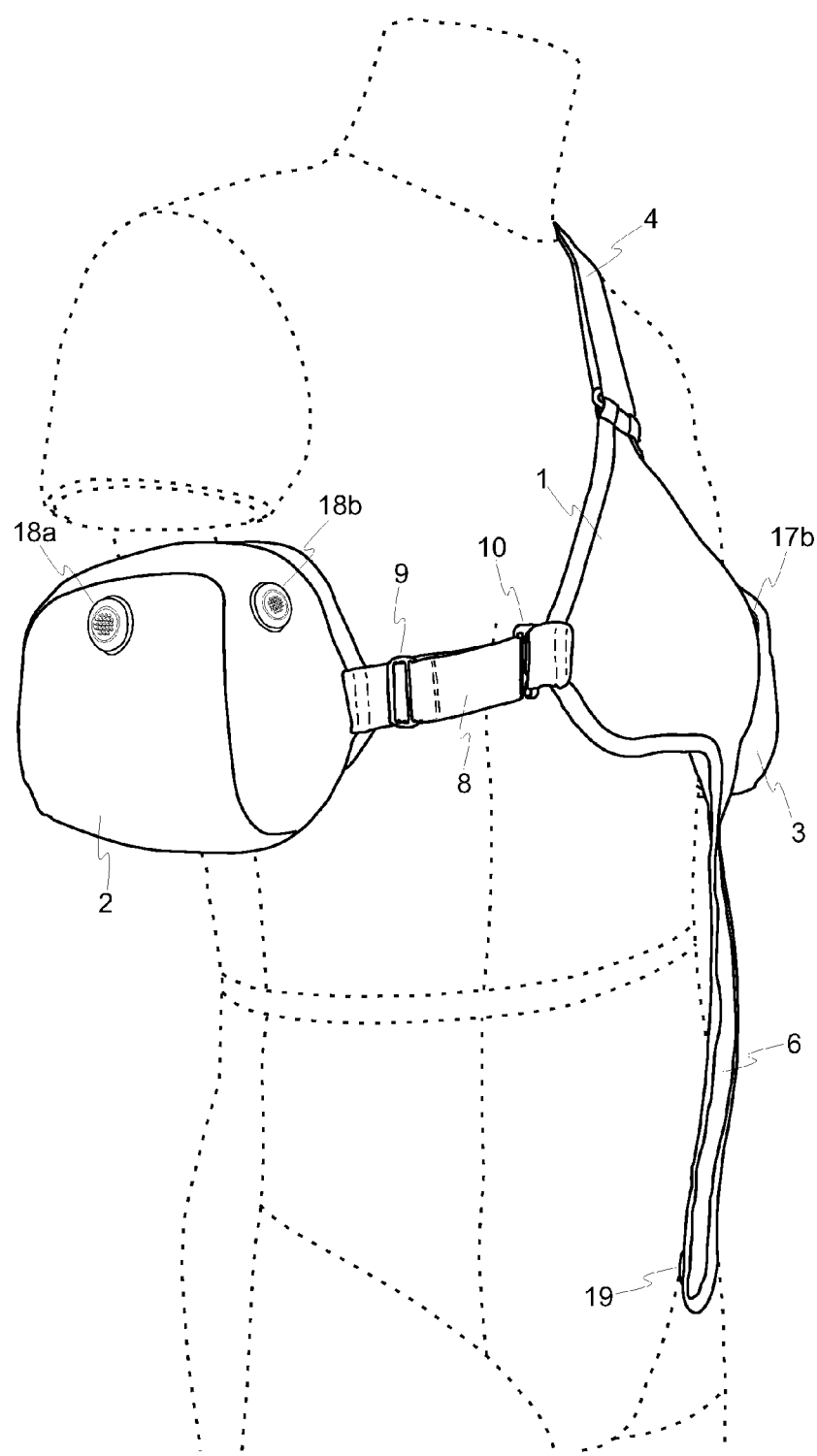
FIG. 3. Three-quarters right side perspective view of the same embodiment of the present invention when worn.
Figure 4:
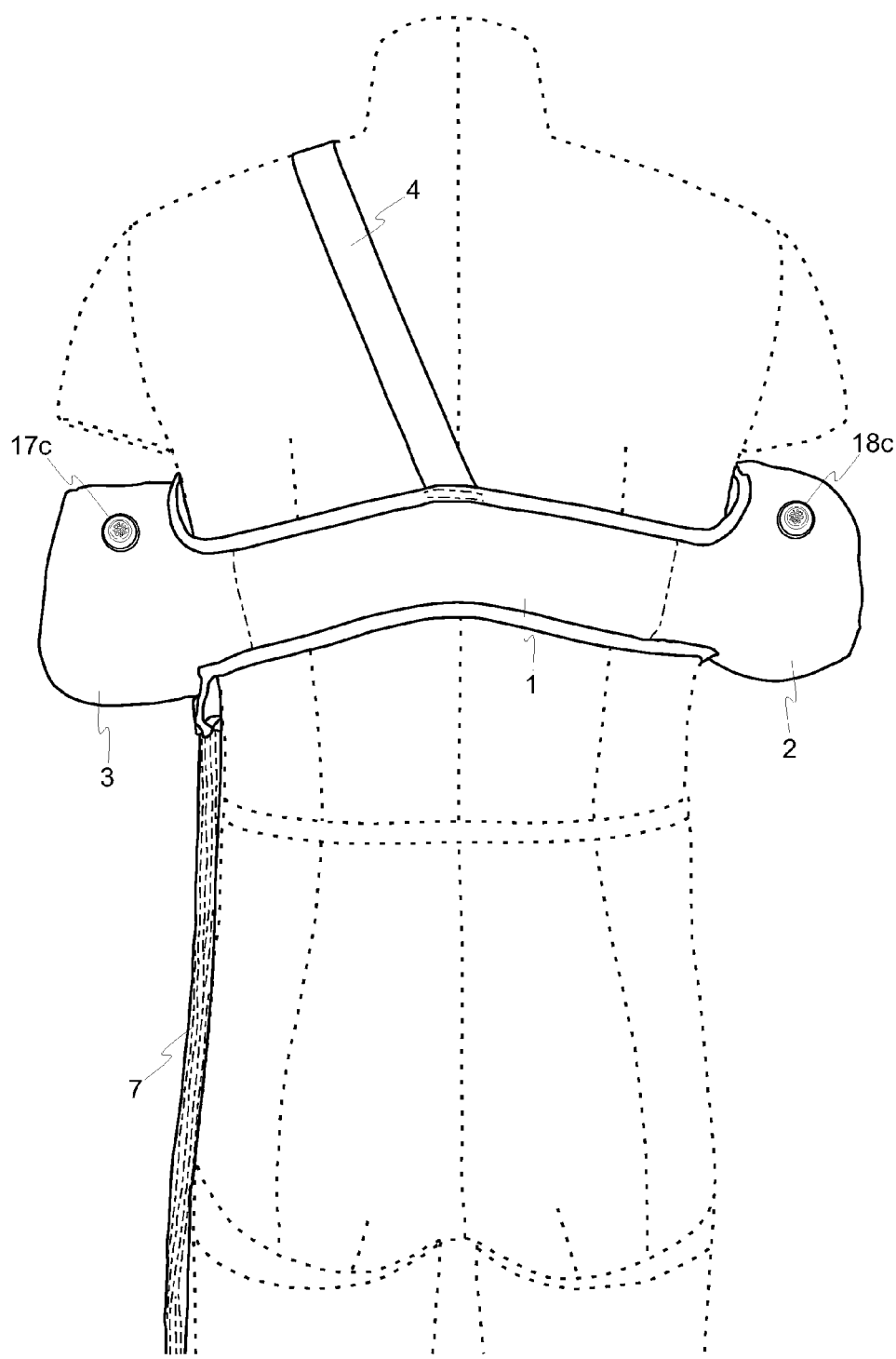
FIG. 4. Back perspective view of the same embodiment of the present invention when worn.
Figure 5:
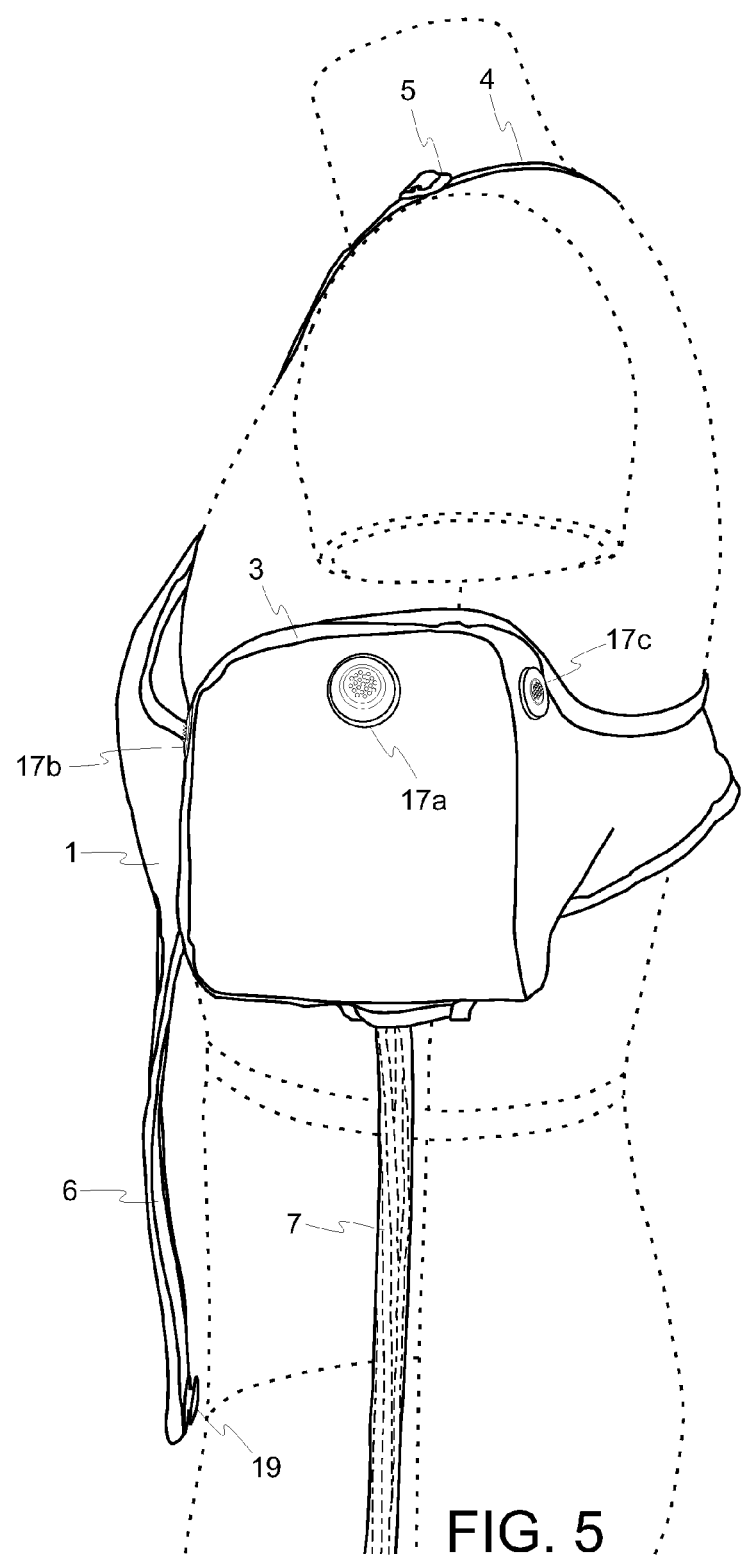
FIG. 5. Left side perspective view of the same embodiment of the present invention when worn.

Attached to the harness are inflatable or padded cushions at the lateral sides of the torso: right cushion 2 supports first RA electrode 18a on its exterior lateral surface (as seen in FIG. 3), second RA electrode 18b on its exterior anterior surface (as seen in FIGS. 1, 2, 3 and 7), and third RA electrode 18c on its exterior posterior surface (as seen in FIG. 4); left cushion 3 supports first LA electrode 17a on its exterior lateral surface (as seen in FIGS. 1, 5, and 7), second LA electrode 17b on its exterior anterior surface (as seen in FIGS. 1, 2, 3, 5, and 7), and third LA electrode 17c on its exterior posterior surface (as seen in FIGS. 4 and 5).

A subject's arms may make contact with these electrodes in one of several different ways. For the RA 18a and LA 17a electrodes, the arms of the subject (not shown) are relaxed downward toward his/her sides and press against the lateral aspects of the cushions which in turn supply pressure for the RA 18a and LA 17a electrodes to abut most typically (or most naturally) against the medial portions of the subject's arms. For the RA 18b and LA 17b electrodes, the arms of the subject are relaxed backward from in front of the cushions and press against the anterior aspects of the cushions which in turn supply pressure for the RA 18b and LA 17b electrodes to abut most typically (or most naturally) against the posterior portions of the subject's arms. For the RA 18c and LA 17c electrodes, the arms of the subject are relaxed forward from in back of the cushions and press against the posterior aspects of the cushions which in turn supply pressure for the RA 18c and LA 17c electrodes to abut most typically (or most naturally) against the anterior portions of the subject's arms. All of these possible configurations provide distal electrode placement and good electrical connection with the given electrode sites. The use of the first RA and LA electrodes 18a and 17a versus second RA and LA electrodes 18b and 17b versus third RA and LA electrodes 18c and 17c depends upon the biomechanical position assumed by the subject or as directed by his/her clinical provider. This choice of which set of RA and LA electrodes to use for the acquisition of the correct corresponding signals may be made in any of a number of ways. One such contemplated way involves simply manually rewiring the electrode wearable prior to use such that the appropriate lead wires are directed to the desired electrodes and not to the unused electrodes. Another such contemplated way involves having the lead wire for a certain desired signal lead, preferably inside the wearable, to multiple alternative electrodes, using a cable splitter; the appropriate signals are then collected by those electrodes which are used and not those which are unused. In other such contemplated ways, each electrode maintains its own separate lead wire and the desired electrodes may be manually selectable either (a) electronically by plugging multiple alternate lead wires into a recording/transmitting/viewing device (not shown) and making the selection between multiple appropriate signals at the recording/transmitting/viewing device or (b) manually by selecting only the desired lead wires among multiple alternate lead wires to plug into the recording/transmitting/viewing device. In another such contemplated way, the selection of the desired electrodes may be performed automatically or assisted in an automated electronic fashion by checking for electrode-skin impedance of the electrodes and by choosing the set of electrodes which, for example, shows the lowest impedance or produces the best signal-to-noise ratio. Various techniques for checking the impedance and signal-to-noise ratios of electrodes are known in the art and any of these techniques may be used.

An adjustable shoulder strap 4, attached to electrode support 1, is adjustable in length by means of an adjustment buckle 5. This shoulder strap need not be undone or disconnected to remove the wearable from the body, thus it does not serve as a single point of disconnect as described earlier in this disclosure.

In the embodiments illustrated in FIGS. 1-7, electrode support 1 further comprises protruding portion 6 which provides connection and support for LL electrode 19, as can be seen in FIGS. 3, 5, 6, and 7. Protruding portion 6 encloses the lead wire for LL electrode 19 and provides extra support and strain relief for this lead wire/electrode while also reducing the risk of disconnection, tangling and knotting associated with a less protected lead wire. In the typical use, the depicted embodiment of the present invention is worn while the subject is bare-chested and preferably while the subject is wearing a relatively tight-fitting garment on the lower part of the body, such as pants with a belt or with a good-fitting or elastic waist or good-fitting or elastic legs, a skirt with a belt or with a good-fitting or elastic waist, or an undergarment that is elastic or has an elastic waist, etc. Protruding portion 6 and LL electrode 19 can then be placed under the waistband etc. of the subject's lower garment with the lower garment's tension about the body supplying the requisite pressure for the LL electrode 19 against the skin of the subject at the electrode site. Padding can also be placed within protruding portion 6, particularly within its distal aspect directly over the top of LL electrode 19, to produce additional downward pressure if needed. Alternately, the LL electrode 19 can be affixed to its site by means of an adhesive collar fixture or by means of a second smaller belt or band (not shown). Adhesive collars of the type disclosed in U.S. patent application Ser. No. 11/454,520 are herein incorporated by reference.

The single-piece construction of the embodiments illustrated makes a 12-or-more-lead ECG easier to self-perform with no possibility for lead wire misplacement and with reduced possibility for mispositioning of electrodes. Proper donning can be easily performed without assistance by slipping the subject's left arm only (if shoulder strap is worn on the left) or head and left arm (if shoulder strap is worn on the right) through the aperture formed by electrode support 1 and shoulder strap 4, followed by self-sizing adjustments, if necessary, at points 5, 8, 9 and 10, either before or after connection at the single point of connection/disconnection 10. Doffing is similarly performed through subsequent disconnection at 10 and then slipping the subject's arm (and head, if shoulder strap 4 is worn on the right) back out the same aperture formed by electrode support 1 and shoulder strap 4.

In the embodiment of the invention illustrated in FIGS. 1-6, the harness serves only to collect ECG signals (or other physiological signals) by means of the electrodes and electrode support 1. In such an embodiment, incoming analog signals from the subject are measured or detected by the electrodes and then transferred to and carried by properly shielded electrode lead wires. The individual lead wires are then gathered together in a bundle or sheath 7, which is preferably also shielded so as to reduce the effect of ambient electromagnetic interference of the type produced by certain lighting fixtures, radio equipment, etc. The lead wires may then be connected at the other end to recording or monitoring equipment, where the signals may be amplified, digitized, multiplexed, processed, stored, viewed, transmitted, retransmitted, etc. In such an embodiment, the invention may interface with either a smaller portable electronic device or a diagnostic ECG cart of the type commonly found in a clinic. Other embodiments, such as the one illustrated in FIG. 7, house one or more electronic components for amplifying, digitizing, multiplexing, storing, and/or transmitting in a wired or wireless fashion the collected physiological signals. In FIG. 7, internal electrode lead wires, instead of exiting the harness through bundle or sheath 7, are connected to electronics 21, which may comprise one or more of amplifiers, filters, A/Ds, multiplexers, microprocessors, transmitters, a battery power source, a display screen (which may be a touch screen), and/or other user controls, including an operable user interface, for collecting, analyzing, storing, and/or transmitting physiological signals from the electrodes in a wired or wireless fashion. Storage may be done in non-volatile flash memory (e.g., on a removable CF card or similar) or by any other means known in the art. Wired or wireless transmission of digital signals may occur by any transmission protocol known in the art.

Electronics 21 may also test for failure or malfunction of electrodes. For example, a signal is output on the lead wire to the electrode or a direct current level associated with the signal from which the electrode is monitored. Electronics 21 test for electrode failure or malfunction and indicates the results. Electronics 21 may also determine whether the biopotential signal is within an expected range. For example, the electronics 21 compare the digital electrode signals, such as after interpolation, to maximum and minimum thresholds. If either threshold is exceeded by a particular number of samples or for a particular time, a lead-off or faulty electrode is indicated. When one or more samples are subsequently within hysteresis limits of the thresholds, then an error is no longer indicated. When a lead-off condition is indicated, the receiver opens an analog switch, or alternatively, does not generate a signal for the output corresponding to the malfunctioning or failed electrode. As a result, the electronics 21 indicate a failure of the electrode by means of its display, an audible alarm, a wirelessly transmitted signal, etc.

As described elsewhere in this disclosure, electrode support 1 preferably also contains padding (not visible in the drawings except as a bulging of the electrode support) which assists in pressing chest electrodes and particularly $V_1$ 11, $V_2$ 12, $V_3$ 13, and $V_3R$ 22 whenever present against the chest and particularly over the sternum, which can be a concave portion on the chest where typical electrode harnesses tend to tent the electrodes. In the embodiment illustrated in FIG. 7 the electronics 21 further serve a mechanical function of working in concert with the padding to assist the push-down of the electrodes against their respective sites and ensure good electrical contact.

FIG. 7 also shows the relative positions of electrodes 11-16 and 19, which are interior to the electrode support 1, as dashed lines.

Figure 8:
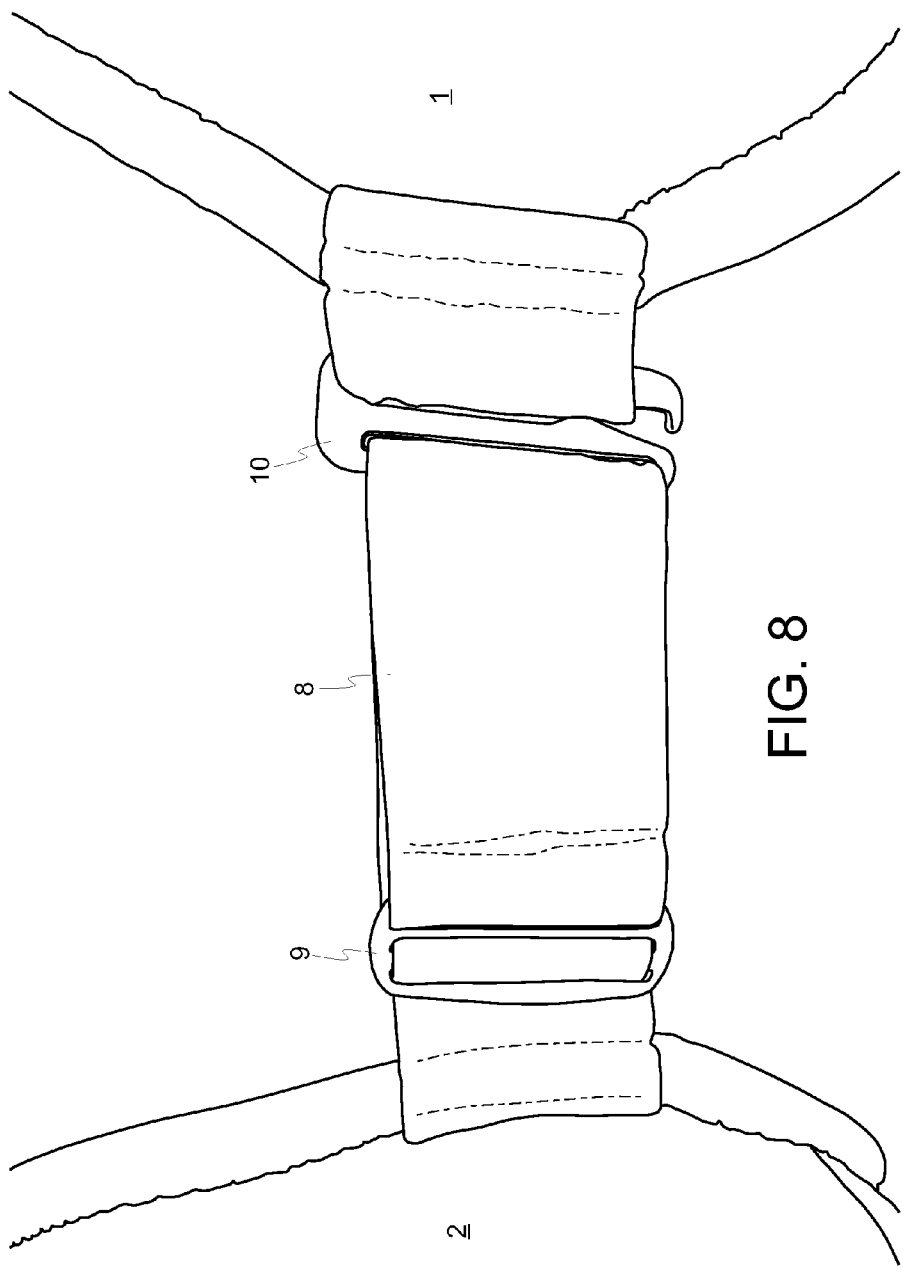
FIG. 8. Magnified perspective view of the adjustable single point of connection/disconnection of the previously-illustrated embodiments of the present invention.

As shown in FIGS. 2 and 3, and in close-up in FIG. 8, the harness of the embodiments of FIGS. 1-9 is preferably connected about the body by the single point of connection comprising a short adjustable fastener 8 comprising adjustment buckle 9 and elongated hook 10. Standard materials associated with, for example, nylon-coated metal bra hooks from Lowy, Inc. can provide sufficient hardware for these fasteners, buckles and hooks.

The adjustability of the shoulder strap 4 and the connection point strap 8 may provide limited sizing for a snug fit, but variations in body size in any given population of individuals are too great for a single harness to provide correct electrode placement and snug comfortable fit to every individual. Therefore, in the illustrated embodiments, the electrode wearable of the present invention is not one-size-fits-all but may be fabricated in several different sizes, e.g., extra small (pediatric), small, medium, large, and extra large so as to comfortably fit and provide correct electrode placement for the greatest portion of a population with varying body sizes.

Figure 10:
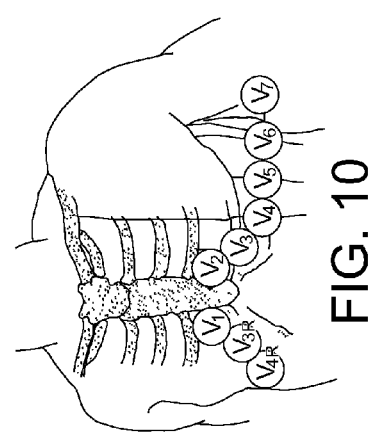
FIG. 10. Diagram showing relative placement of chest-abutting electrodes in pediatric or other specialized embodiment of the wearable of the present invention.

FIG. 9 illustrates another embodiment of the invention adapted to add more electrodes for a 15-lead ECG. Particularly when such an embodiment is adapted for pediatric use, the wearable may be sized smaller overall than the embodiment(s) illustrated in the other drawings but will preferably have additional room on the harness to house $V_{3R}$ electrode 22 and $V_{4R}$ electrode 23. This embodiment will also preferably add $V_7$ electrode 24. The relative placements of these electrodes on the chest is illustrated in the diagram of FIG. 10: $V_1$ is placed at the fourth intercostal space at the right border of the sternum; $V_2$ is placed at the fourth intercostal space at the left border of the sternum; $V_3$ is placed midway between locations $V_2$ and $V_4$; $V_3R$ is placed midway between locations $V_1$ and $V_{4R}$; $V_4$ is placed at the mid-clavicular line in the fifth intercostal space to the left of the sternum; $V_{4R}$ is placed at the mid-clavicular line in the fifth intercostal space to the left of the sternum; $V_5$ is placed at the anterior axillary line on the same horizontal level as $V_4$; $V_6$ is placed at the mid-axillary line on the same horizontal level as $V_4$ and $V_5$; and $V_7$ is placed at the posterior axillary line on the same horizontal level as $V_4$, $V_5$, and $V_6$.

Depending on the embodiment the harness and/or electrodes of the present invention can be either reusable or disposable.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed is:

1. A wearable for administration or self-administration of a resting 12-or-more-lead ECG from full or reduced electrode sets, of a subject having arms and a body, the wearable comprising:
    a thin flexible electrode support adapted to be worn only about the subject's torso and having an inside in contact with the subject's torso and an outside, the support further supporting a plurality of electrodes, including at least one precordial electrode and LA, RA, and LL electrodes, and
    electrode-supporting cushions attached to or integral to the outside of the electrode support with the LA and RA electrodes attached to or integrated into the electrode-supporting cushions, the cushions placed on the electrode support such that pressure is exerted by the cushions upon the arms when the arms are placed in contact with the cushions directed downwardly in either a sideward, backward or forward direction, the pressure being sufficient to make the cushion-mounted LA and RA electrodes contact with the medial, posterior or anterior surfaces of the arms without substantial muscular exertion on the part of the subject to press the arms into the cushion-mounted LA and RA electrodes.

2. The wearable of claim 1, wherein the electrodes are dry electrodes.

3. The wearable of claim 1, wherein the wearable comprises at least one adjustable shoulder strap.

4. The wearable of claim 1, wherein the wearable is configured to be fastened about the subject's torso only by no more than one point of connection/disconnection.

5. The wearable of claim 4, comprising one point of connection/disconnection, said point of connection/disconnection comprising a fastener of adjustable length to resize or adjust tightness so as to provide a good fitting of the wearable to the subject.

6. The wearable of claim 1, wherein the LA, RA and LL electrodes are arranged according to a Lund or modified Lund electrode placement scheme.

7. The wearable of claim 1, wherein the wearable further comprises electronic components embedded in the thin flexible electrode support that amplify, digitize, multiplex, store, and/or transmit signals from the electrodes, and said electronic components also mechanically function, along with padding in the thin flexible electrode support, to supply pressure on electrodes including the at least one precordial electrode, against the chest.

8. A wearable for administration or self-administration of a resting 12-or-more-lead ECG from full or reduced electrode sets, of a subject having a chest having a sternum, the wearable comprising:
    a thin flexible electrode support adapted to be only worn upon a subject's torso having an inside in contact with the subject's torso and an outside, the support further supporting a plurality of electrodes, including at least one precordial electrode and LA, RA, and LL electrodes, each electrode having a respective placement site, the thin flexible electrode support comprising padding in the thin flexible support over the sternum such that any electrodes subject to tenting near the sternum are pushed down toward the chest, bringing them into good electrical contact with their respective placement sites; and
    wherein no adhesives are used in fastening the wearable, electrode support, or any electrodes to the subject.

9. The wearable of claim 8, wherein the electrodes are dry electrodes.

10. The wearable of claim 8, wherein the wearable is configured to be fastened about the subject's torso only by no more than one point of connection/disconnection.

11. The wearable of claim 10, comprising one point of connection/disconnection, said point of connection/disconnection comprising a fastener of adjustable length to resize or adjust tightness so as to provide a good fitting of the wearable to the subject.

12. A single-piece wearable for administration or self-administration of a resting 12-or-more-lead ECG from full or reduced electrode sets on a subject having arms and a body, the single-piece wearable comprising:
    a thin flexible electrode support adapted to be only worn upon the subject's torso, the support having an inside adapted to be in contact with the subject's torso and an outside, the support further supporting a plurality of electrodes, including at least one precordial electrode located on the support to be on the subject's chest when the support is worn by the subject, and LA, RA, and LL electrodes, the LA and RA electrodes disposed to make contact with the medial, posterior or anterior aspects of the subject's arms, without the use of any adhesive on the subject's body, without additional belts, bands, gloves, or bracelets other than what is provided in the thin flexible electrode support,
    wherein the thin flexible electrode support has one point of connection/disconnection configured to fasten the support around the subject's torso.

13. The wearable of claim 12, wherein the electrodes are dry electrodes.

14. The wearable of claim 12, wherein the wearable is fastened about the subject's torso by no more than one point of connection/disconnection, and the point of connection/disconnection comprises a fastener of adjustable length to resize or adjust tightness so as to provide a good fitting of the wearable to the subject.

15. The wearable of claim 14, comprising one point of connection/disconnection wherein the fastener comprises an elongated hook.

16. The wearable of claim 12, wherein the electrodes are arranged according to a Lund or modified Lund electrode placement scheme.

17. The wearable of claim 16, wherein the wearable further comprises electrode-supporting cushions attached to or integral to the outside of the electrode support, upon which the LA and RA electrodes are mounted, attached or integrated into, the cushions being disposed on the electrode support such that pressure is exerted by the cushions upon downward-resting arms when the arms are in contact with the cushions directed in a sideward, backward or forward direction, the pressure being sufficient to make the cushion-mounted LA and RA electrodes contact with the medial, posterior or anterior surface of the arms without substantial muscular exertion on the part of the subject to press the arms into the cushion-mounted LA and RA electrodes.

18. The wearable of claim 17, wherein the subject's chest comprises a sternum and the thin flexible electrode support comprises padding in the thin flexible support over the sternum such that any electrodes subject to tenting near the sternum are pushed down toward the chest, bringing them into good electrical contact with their respective sites.

19. The wearable of claim 18, wherein the wearable further comprises electronic components embedded in the thin flexible electrode support that amplify, digitize, multiplex, store and/or transmit signals from the electrodes, and said electronic components also mechanically function, along with the padding in the thin flexible electrode support, to supply pressure on electrodes including the at least one precordial electrode, against the chest.

\* \* \* \* \*